US005396896A

United States Patent [19]

Tumey et al.

[11] Patent Number: 5,396,896

[45] Date of Patent: Mar. 14, 1995

[54] MEDICAL PUMPING APPARATUS

[75] Inventors: David M. Tumey; Abdou F. Aboujaoude, both of Dayton; Jonathon W. Reeves, Yellow Springs; David B. McQain, Dayton; William H. Reeves, Spring Valley, all of Ohio

[73] Assignee: Chrono Dynamics, Ltd., Dayton, Ohio

[21] Appl. No.: 700,500

[22] Filed: May 15, 1991

[51] Int. Cl.⁶ .......................... A61B 5/02; A61H 7/00

[52] U.S. Cl. .................................... 128/690; 601/150; 601/152; 601/148

[58] Field of Search ................. 128/690, 680, 64, 630, 128/671, 38–40, 64, 637, 670, 672, 691, 694

[56] References Cited

U.S. PATENT DOCUMENTS

| | | | |
|---|---|---|---|
| 1,492,514 | 2/1920 | Jensen | 128/24 R |
| 1,608,239 | 11/1926 | Rosett . | |
| 2,531,074 | 11/1950 | Miller . | |
| 2,694,395 | 11/1954 | Brown | 128/38 |
| 2,880,721 | 4/1959 | Corcoran | 128/39 |
| 2,893,382 | 7/1959 | Demeny et al. . | |
| 3,171,410 | 3/1965 | Towle et al. | 128/155 |
| 3,403,673 | 10/1968 | MacLeod | 128/40 |
| 3,525,333 | 8/1970 | Mencacci | 128/24.2 |
| 3,774,598 | 6/1973 | Wilson et al. . | |
| 3,811,431 | 5/1974 | Apstein | 128/64 |
| 3,824,992 | 7/1974 | Nicholson et al. | 128/24 R |
| 3,826,249 | 7/1974 | Lee et al. | 128/24 R |
| 3,835,845 | 9/1974 | Maher . | |
| 3,859,989 | 1/1975 | Spielberg | 128/24 R |
| 3,865,102 | 2/1975 | Birtwell et al. | 128/64 |
| 3,865,103 | 2/1975 | Folman | 128/64 |
| 3,866,604 | 2/1975 | Curless et al. | 128/64 |
| 3,888,242 | 6/1975 | Harris et al. | 128/24 R |
| 3,892,229 | 7/1975 | Taylor et al. | 128/24 R |
| 3,908,642 | 9/1975 | Vinmont | 128/40 |
| 3,920,006 | 11/1975 | Lapidus | 128/24.1 |
| 3,942,518 | 3/1976 | Tenteris et al. . | |
| 3,976,056 | 8/1976 | Brawn | 128/24 R |
| 3,982,531 | 9/1976 | Shaffer | 128/24 R |
| 3,993,053 | 11/1976 | Grossan | 128/64 |
| 4,044,759 | 8/1977 | Ghayouran | 128/24 R |
| 4,054,129 | 10/1977 | Byars et al. | 128/24 R |
| 4,077,402 | 3/1978 | Benjamin et al. | 128/64 X |
| 4,091,804 | 5/1978 | Hasty | 128/24 R |
| 4,153,050 | 5/1979 | Bishop et al. | 128/64 |

(List continued on next page.)

FOREIGN PATENT DOCUMENTS

| | | |
|---|---|---|
| 2157192 | 6/1973 | France . |
| 2390156 | 1/1979 | France . |
| 2430651 | 1/1976 | Germany . |
| 2716137 | 7/1978 | Germany . |
| 4286 | of 1896 | United Kingdom . |
| 233387 | 5/1925 | United Kingdom . |
| 473639 | 10/1937 | United Kingdom . |
| 479261 | 2/1938 | United Kingdom . |
| 490341 | 8/1938 | United Kingdom . |
| 754883 | 8/1956 | United Kingdom . |
| 2050174B | 1/1981 | United Kingdom . |
| 2055580A | 3/1981 | United Kingdom . |

(List continued on next page.)

OTHER PUBLICATIONS

Derek F. Stubbs, Neuro Computers.

Parrott, J., "The Effect of a Mechanical Kenous Pump on the Circulation in the Feet in the Presence of Arterial Obstruction", University of Manitoba, Oct. 1972.

Venous Pump of the Human Foot Preliminary Report; Gardner et al. Jul. 1983.

Hemo Flo-Intermittent Compression Medipedic.

Flowtron Air.

*Primary Examiner*—Robert A. Hafer

*Assistant Examiner*—Brian E. Hanlon

*Attorney, Agent, or Firm*—R. William Graham; H. Stanley Muir

[57] ABSTRACT

This invention relates to a medical pumping apparatus which utilizes a neural network. The medical pumping apparatus continuously and automatically monitors fill status of the venous plexus and flow rate from the venous plexus and continuously and automatically controls the pressure and cycle rate of a pump capable of cyclically applying pressure to a part of the human body for the purpose of maximizing blood transfer therein.

36 Claims, 2 Drawing Sheets

U.S. PATENT DOCUMENTS

| | | | |
|---|---|---|---|
| 4,186,732 | 2/1980 | Christoffel | 128/24 R |
| 4,198,961 | 4/1980 | Arkans | 128/24 R |
| 4,202,325 | 5/1980 | Villari et al. | 128/24 R |
| 4,206,751 | 6/1980 | Schneider | 128/24 R |
| 4,207,876 | 6/1980 | Annis | 128/24 R |
| 4,231,355 | 11/1980 | Hara | 128/24.2 |
| 4,269,175 | 5/1981 | Dillon | 128/24 R |
| 4,311,135 | 1/1982 | Brusckner et al. | 128/24 R |
| 4,370,975 | 2/1983 | Wright | 128/64 |
| 4,372,297 | 2/1983 | Perlin | 128/64 |
| 4,374,518 | 2/1983 | Villanova | 128/64 |
| 4,402,312 | 9/1983 | Villari et al. | 128/24 R |
| 4,418,690 | 12/1983 | Mummert | 128/24 R |
| 4,453,538 | 6/1984 | Whitney | 128/24 R |
| 4,461,301 | 7/1984 | Ochs | 128/630 |
| 4,502,470 | 3/1985 | Kiser et al. . | |
| 4,519,395 | 5/1985 | Hrushesky | 128/671 |
| 4,574,812 | 3/1986 | Arkans | 128/691 |
| 4,577,626 | 3/1986 | Marukawa et al. . | |
| 4,624,244 | 11/1986 | Taberi . | |
| 4,702,232 | 10/1987 | Gardner et al. | 128/64 |
| 4,753,226 | 6/1988 | Zheng et al. | 128/64 |
| 4,809,684 | 3/1989 | Gardner et al. . | |
| 4,841,956 | 6/1989 | Gardner et al. | 128/64 |
| 4,846,160 | 7/1989 | Gardner et al. . | |
| 4,858,147 | 8/1989 | Conwell | 364/513 |
| 4,974,597 | 12/1990 | Walloch | 128/680 |
| 4,993,420 | 2/1991 | Welkowitz et al. | 128/691 X |
| 5,014,714 | 5/1991 | Millay et al. | 128/672 |
| 5,060,279 | 10/1991 | Crawford et al. | 395/22 |
| 5,090,417 | 2/1992 | Mollan et al. | 128/691 |
| 5,099,851 | 3/1992 | Hata et al. | 128/672 |

FOREIGN PATENT DOCUMENTS

| | | |
|---|---|---|
| 2103489 | 2/1983 | United Kingdom . |
| 2077108B | 3/1984 | United Kingdom . |
| 2141938 | 1/1985 | United Kingdom . |
| 813352 | 5/1989 | United Kingdom . |
| 8911845 | 12/1989 | WIPO . |
| 9103979 | 4/1991 | WIPO . |

MEDICAL PUMPING APPARATUS

This invention relates to a medical apparatus and more particularly, but not by way of limitation, to a medical apparatus for continuously and automatically monitoring fill rate of the venous plexus and flow rate from the venous plexus and for continuously and automatically controlling pressure and cycle rate of a pump capable of cyclically applying pressure to a part of the human body for the purpose of maximizing blood transfer therein.

It is well known that thromboembolism, pulmonary emboli, ischemia and other diseases result from the occluding of vessels within mammalian tissue. Various factors are known to contribute to such diseases. For example, some of the factors include (negative intrathoracic pressure), gravity, lack of muscular activity and muscular tone, vein obstruction, and age of the patient.

Previously, pumping apparatuses have been used on a part of the human body for the purpose of increasing and/or stimulating blood flow. Such apparatuses have been made to adapt to an arm, hand, leg, foot, etc. The apparatuses typically include an inflatable bag connected to a pump capable of delivering sufficient pressure with the bag to cause stimulation. Some apparatuses inflate and deflate in a cyclical fashion. The cycle rates and pressure are typically manually set by a clinician who audibly determines the blood flow from the venous plexus to the major veins with a Doppler monitor.

One device employs the inflatable bag solely to the plantar-arch region of the foot. A particular disadvantage of the device is that it lacks the ability to maximize the accuracy and efficiency with which pressure is being applied to the body part. A clinician is required to continuously observe the patient's condition in order to assure that the pressure and cycle rate is set to maintain an optimum blood flow rate.

Another apparatus provides an automated pumping system by synchronizing the pumping with the heart beat and/or blood flow in a part of the body distal from the body part to which pressure is being applied. Such system fails to provide an accurate means for detecting the maximum blood fill status in the body part to which pressure is applied.

Previous apparatuses fail to consistently and accurately synchronize pressure application with the maximum blood fill status in the tissue. The inflation impulse may be premature, simultaneous with or subsequent to the maximum fill status. If such impulse occurs during the absence of blood, the pressure applied to such site causes pain in certain patients.

It is thought that there exists a natural pumping mechanism in the foot which occurs while walking and which aids circulation. This pumping mechanism becomes inactive for a person in a supine or non-weight bearing position. For some non-weight bearing persons, such as bed ridden patients, this pumping mechanism can be inactive for extended periods of time.

In non-weight bearing conditions, arterial flow to the micro vascular bed is decoupled from venous outflow. This is because capillaries are passive collapsible tubes with only about one in six open at any one time thus leading to the potential complications associated with ischemia.

The muscles which interconnect the ball and heel of the foot are intrinsically involved in this pumping mechanism. Weight bearing pressure upon the heel and ball of the foot causes the muscles to contract to prevent flattening of the arch of the foot. This muscle contraction aids the emptying of blood from the foot.

While the existing foot pumping apparatus applies pressure to the region of the foot solely between the ball and heel of the foot, the apparatus fails to simulate this natural pumping mechanism. This is because insufficient pressure is applied to the ball and heel of the foot. The previous system also tends irritate the heel and dorsal aspect of the foot. This is because the means used to hold the inflatable bag in the plantar arch tends to rub and irritate certain areas of the foot.

There is therefore a need for an apparatus which can continuously and automatically determine the fill status of the body part to which pressure is applied. There is a need for an apparatus which continuously and automatically adjusts the pressure and cycle rate according to such status. There is a need for an apparatus which simulates the natural pumping mechanism which occurs while walking. A need also exists for an apparatus which can be worn for extended periods of time without irritating the foot. In addition, there exists a need for a device capable of monitoring the therapeutic effect of such pumping apparatus.

SUMMARY OF THE INVENTION

It is an object of the present invention to provide a medical pumping apparatus which is responsive to and controlled by the patient's physiological condition.

It is an object of the present invention to provide a medical pumping apparatus which continuously and automatically determines blood fill status in a part of the human body and applies pressure to such part in a cyclical fashion, rate and duration in accordance with such fill status for the purpose of maximizing circulation.

It is still another object to pump the maximum amount of blood in a given body part at any given time. These sudden changes (hemodynamics shear-stress) within the venous system liberates Endothelial-Derived Relaxing Factor (EDRF), a powerful relaxation of vascular smooth muscle. The process of EDRF causes additional capillaries to open with the increase in blood flow thus causing a rapid relief of ischemic rest pain, reducing in swelling, restoration of tissue viability and decreased healing time in the body.

It is yet another object of the present invention to provide a medical pumping apparatus adapted to fit the human foot which simulates the natural pumping mechanism which occurs while walking.

Accordingly, the present invention is directed to a medical apparatus comprising means for cyclically applying pressure to a part of the human body, means for continuously sensing blood fill status in the body part and generating a signal in response thereto, means for receiving and manipulating the signal to produce a generalization about the signal and means operatively associated with the receiving and manipulating means for controlling the pressure means in accordance with the generalization. The present invention also includes means operatively connected to the receiving and manipulating means for continuously sensing blood fill rate and generating a signal in response thereto.

In the preferred embodiment, the receiving and manipulating means is a neural network having solution space memory indicative of needing to increase, decrease, or maintain pressure; solution space memory indicative of needing to increase, decrease or maintain cycle rate; and solution space memory indicative of normal and abnormal physiological conditions. The neural network performs the generalization by projecting the signal into at least one of the solution space memories.

The pressure means comprises an inflatable boot and pumping apparatus operatively connected to the boot. The control means is a control circuit which is responsive to the neural network and which controls the delivery of pneumatic pressure by the pumping apparatus.

The boot includes an inflatable bladder shaped to conform to the human foot, a plate connected to the bladder and adapted to longitudinally extend along the sole of the foot, a surface conformable member disposed on the plate and positioned to conform to the sole of the foot, valve means integrally formed with the bladder through which the pneumatic pressure passes, and means for securing the boot to the foot

DETAILED DESCRIPTION OF THE PREFERRED EMBODIMENT

DEFINITION

"Cyclical" or "cyclically", as used with respect to the present invention only, shall be defined as having a variable periodicity which is a function of physiological conditions; i.e., the variables periodicity shall be determined by the varying refill rates of the vascular bed as calculated by a neural network described hereinafter.

Figure 1:
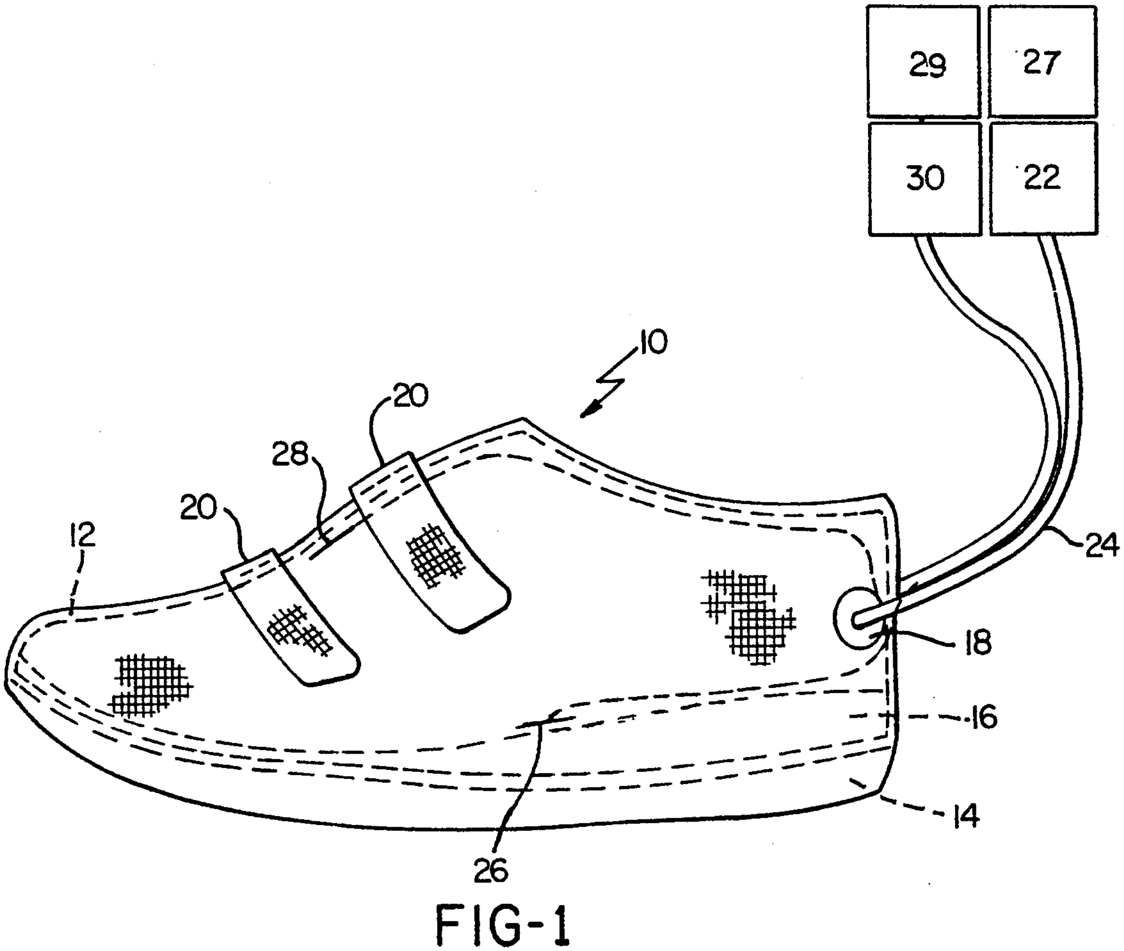
FIG. 1 is a side view of an inflatable boot, as associated with a pumping apparatus, sensors and a neural network.

The inflatable boot 10 is best depicted in FIG. 1. The boot 10 includes an inflatable bladder 12 shaped to conform to the foot. The bladder 12 can be made of a single flexible nonpuncturable material which is enveloped and peripherally sealed or made of two separate flexible nonpuncturable materials of substantially the same size and shape and peripherally sealed. The bladder 12 is preferably made of a non-allergenic polyvinyl chloride or polyurethane film. In addition, a slip resistant material is preferably used for the sole of the boot. The boot 10 is adaptable to either the right or the left foot (by design).

The boot 10 further includes a plate 14 which is connected to the bladder 12 such that the plate 14 longitudinally extends between the bladder 12 and the sole of the foot. The plate 14 can be made of any rigid or semi-rigid material, such as metal or plastic.

The boot 10 also includes a surface conformable member 16 disposed on the plate 14 and positioned to substantially conform to the entire sole of the foot. The member 16 is preferably a fluid or semifluid made of a material such as SILASTIC TM housed within a nonpuncturable material. Alternatively, the member 16 can be an air inflated nonpuncturable material.

The boot 10 also includes a valve 18 integrally formed with the bladder 12 through which the pneumatic pressure passes, and means 20 for securing the boot 10 to the foot. The securing means 20 may be a fastener, such as a belt and buckle, or a VELCRO TM flap.

As depicted in FIG. 1, pump apparatus 22 is connected to the valve 18 via conduit 24 so that bladder 12 can be inflated. The pump apparatus 22 is capable of delivering cyclical pneumatic pressure to the bladder 12. When the bladder 12 is inflated, the boot 10 applies a weight bearing like pressure to the foot. In this respect, the surface conformable member 16 is substantially coextensive with the entire sole of the foot and exerts pressure thereagainst. Thus, pressure is applied to the heel, ball and plantar aspect of the foot in a manner similar to that which occurs while walking.

As seen in FIG. 1, the sensors 26 and 28 are operatively associated with the boot 10 and a neural network 30, described herein below, for sensing resistive impedance across the foot and generating a signal in response thereto. For example, the impedance sensors can be a self-sticking electrodes which are constructed using a self adhering conductive gel. The sensors can be of any suitable conductive material, such as metal, e.g. silver.

Alternatively, the sensors can be for sensing the capacitive dielectric between the top and bottom of the patients foot. It is to be noted that the dielectric constant is partly a dependent function of the amount of blood (and electrolytes) present in the foot at a given point in time. When blood is forced out of the foot, (by pressure), the impedance changes dramatically. When blood is allowed to refill the venous plexus into the foot, the impedance changes slowly until reaching a steady state point where it is assumed that substantially maximum blood fill status is achieved. At approximately the steady state point, the pneumatic pressure is delivered. The sensor 26 is connected to a central portion of the surface conformable member 16 and is disposed adjacent to and between the sole of the foot and the member 16. The sensor 28 is connected to the bladder 12 and positioned adjacent the dorsum of the foot. Other electrode locations are possible. For example, the electrodes can be placed at the front and back of the foot separated by a sufficient distance to maximize sensitivity, generally about 3–4 inches. The areas to which the electrodes are being attached should be abraded first to ensure good contact. Several methods for determining the impedance of the circuit can be employed, including a bridge arrangement, where the effective capacitor is placed in relation to some known values.

Also, a rate sensor 27 can be mounted in such a way to monitor the blood profusion of the venous plexus, or mounted to some part of the foot, such as the toe, to monitor the fill status of the plexus. A blood flow rate sensor 27 can be mounted somewhere near the calf of the leg, perhaps, of an individual undergoing treatment.

Additionally, optical sensors such as light reflective rheology sensors 29 are positioned adjacent to the foot or calf to quantitatively sense filling of the subcutaneous micro vasuclar bed and generate a signal in response thereto. Such sensors are operatively connected to the neural network 30 to aid in the detection of deep vein thrombosis as well as a wide range of problems associated with ischemia and venous insufficiency and indicate the need for additional diagnostic testing.

A device operatively connected to the neural network can be provided for the patient to actuate when sensing pain. In this respect, the patient can manually input into the neural network to adjust the action of the pumping apparatus.

A biological information input (not shown) operatively connected to the neural network is also provided for the doctor utilizing the apparatus. As will be discussed below, the neural network utilizes such input to effect the operation of the pumping apparatus.

Figure 2:
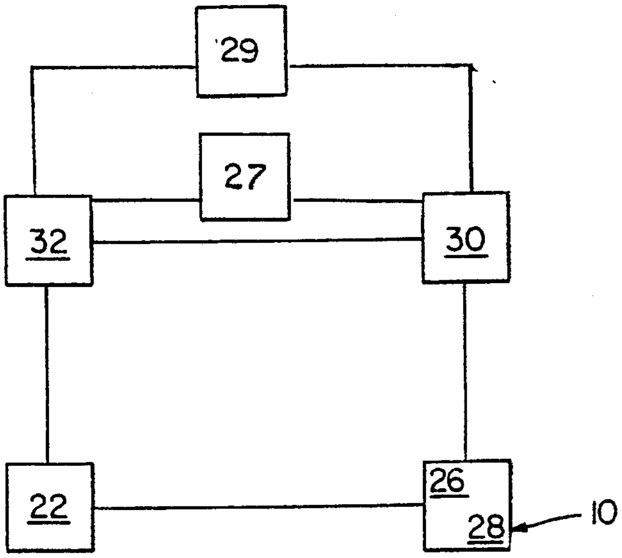
FIG. 2 is a block diagram of the medical pumping apparatus.

FIG. 2 shows a control circuit 32 which is operatively associated with the neural network 30 and controls the pump apparatus 22, which in turn operates the boot 10. The neural network 30 is receptively connected to sensors 26 and 28. The control circuit 32 can be a commercially available microprocessor which uses the software system described herein below. Alternatively, a commercially available microprocessor can be integrated with a commercially available neurocomputer accelerator board, such as the one available from Science Applications International Corp. (SAIC).

Optionally, a display can be connected to the control circuit or neural network such that the projected signal can be displayed. The display would provide a visual aid to observe the various output signals, such as pressure, cycle rate, and physiological condition.

Figure 3:
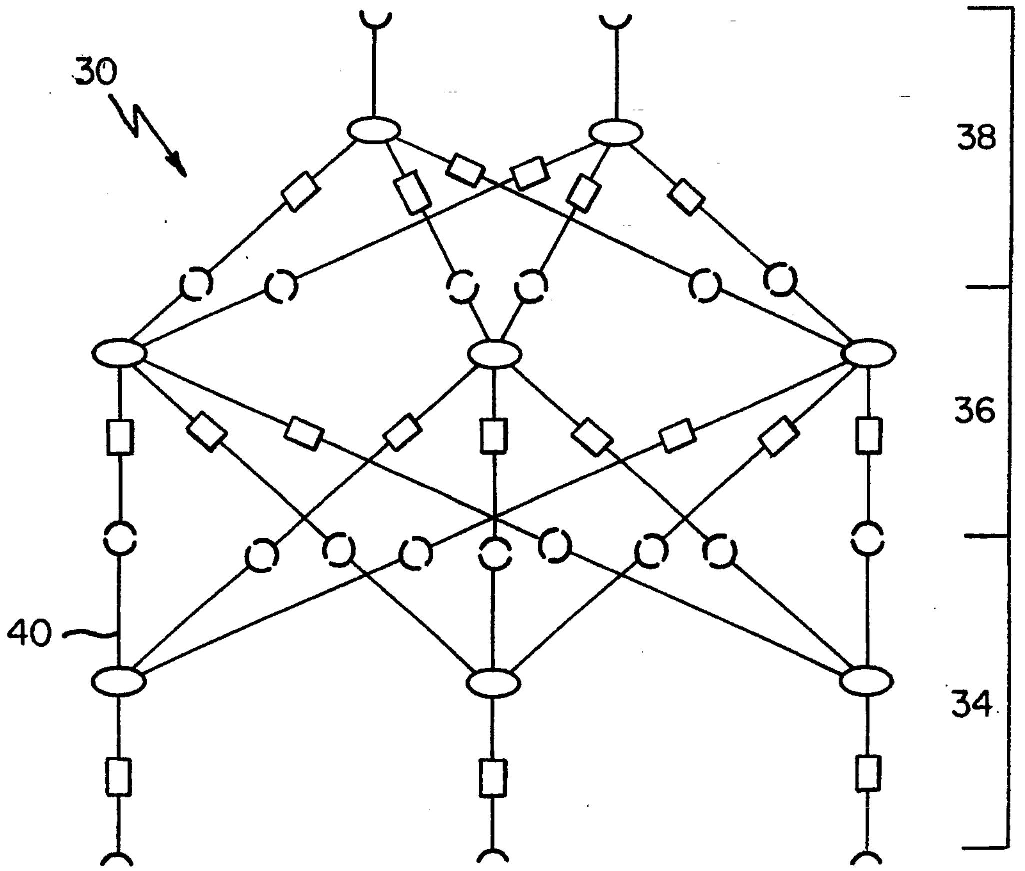
FIG. 3 is a representation of the three layer neural network which is used in the invention.

As shown in FIG. 3, the neural network 30 includes at least one layer of trained neuron-like units, and preferably at least three layers. The neural network 30 includes input layer 34, hidden layer 36, and output layer 38. Each of the input, hidden, and output layers include a plurality of trained neuron-like units 40.

Neuron-like units can be in the form of software or hardware. The neuron-like units of the input layer include a receiving channel for receiving a sensed signal, wherein the receiving channel includes a predetermined modulator for modulating the signal.

The neuron-like units of the hidden layer are individually receptively connected to each of the units of the input layer. Each connection includes a predetermined modulator for modulating each connection between the input layer and the hidden layer. The neuron-like units of the output layer are individually receptively connected to each of the units of the hidden layer. Each connection includes a predetermined modulator for modulating each connection between the hidden layer and the output layer. Each unit of said output layer includes an outgoing channel for transmitting the modulated signal.

Figure 4:
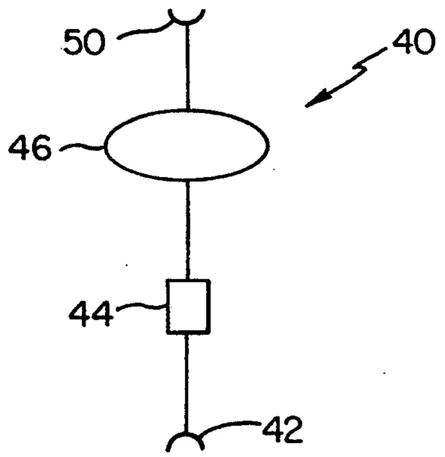
FIG. 4 is a representation of a neuron-like unit.

Referring to FIG. 4, Each trained neuron-like unit 40 includes a dendrite-like unit 42, and preferably several, for receiving analog incoming signals. Each dendrite-like unit 42 includes a particular modulator 44 which modulates the amount of weight which is to be given to the particular characteristic sensed. In the dendrite-like unit 42, the modulator 44 modulates the incoming signal and subsequently transmits a modified signal. For software, the dendrite-like unit 42 comprises an input variable $X_a$ and a weight value $W_a$ wherein the connection strength is modified by multiplying the variables together. For hardware, the dendrite-like unit 42 can be a wire, optical or electrical transducer having a chemically, optically or electrically modified resistor therein.

Each neuron-like unit 40 includes soma-like unit 46 which has a threshold barrier defined therein for the particular characteristic sensed. When the soma-like unit 46 receives the modified signal, this signal must overcome the threshold barrier whereupon a resulting signal is formed. The soma-like unit 46 combines all resulting signals and equates the combination to an output signal necessitating either an increase, decrease or maintaining of pressure and cycle rate, and/or indicates normal or abnormal physiological conditions. For software, the soma-like unit 46 is represented by the sum $=\Sigma_a X_a W_a - \beta$, where $\beta$ is the threshold barrier. This sum is employed in a Nonlinear Transfer Function (NTF) as defined below. For hardware, the soma-like unit 46 includes a wire having a resistor; the wires terminating in a common point which feeds into an operational amplifier having a nonlinearity part which can be a semiconductor, diode, or transistor.

The neuron-like unit 40 includes an axon-like unit 48 through which the output signal travels, and also includes at least one bouton-like unit 50, and preferably several, which receive the output signal from axon-like unit 48. Bouton/dendrite linkages connect the input layer to the hidden layer and the hidden layer to the output layer. For software, the axon-like unit 48 is a variable which is set equal to the value obtained through the NTF and the bouton-like unit 50 is a function which assigns such value to a dendrite-like unit of the adjacent layer. For hardware, the axon-like unit 48 and bouton-like unit 50 can be a wire, an optical or electrical transmitter.

The modulators of the input layer modulate the amount of weight to be given blood flow rate, blood fill rate for the monitored area, muscular condition of tissue, age, position of the patient and pain felt by the patient. For example, if a patient's blood fill rate is higher than, lower than, or in accordance with what has been predetermined as normal, the soma-like unit would account for this in its output signal and bear directly on the neural network's decision to increase, decrease, or maintain pressure and/or cycle rate. The modulators of the output layer modulate the amount of weight to be given for increasing, decreasing, or maintaining pressure and/or cycle rate, and/or indicating a normal or an abnormal physiological condition. It is not exactly understood what weight is to be given to characteristics which are modified by the modulators of the hidden layer, as these modulators are derived through a training process defined below.

The training process is the initial process which the neural network must undergo in order to obtain and assign appropriate weight values for each modulator. Initially, the modulators and the threshold barrier are assigned small random non-zero values. The modulators can be assigned the same value but the neural network's learning rate is best maximized if random values are chosen. Empirical input data are fed in parallel into the dendrite-like units of the input layer and the output observed.

The NTF employs in the following equation to arrive at the output:

$$NTF = \frac{1}{[1 + e^{-*}]}$$

For example, in order to determine the amount weight to be given to each modulator for pressure changes, the NTF is employed as follows:

If the NTF approaches 1, the soma-like unit produces an output signal necessitating an increase in pressure. If the NTF is within a predetermined range about 0.5, the soma-like unit produces an output signal for maintaining pressure. If the NTF approaches 0, the soma-like unit produces an output signal necessitating a decrease in pressure. If the output signal clearly conflicts with the known empirical output signal, an error occurs. The weight values of each modulator are adjusted using the following formulas so that the input data produces the desired empirical output signal.

For the output layer:

$W^*_{kol}=W_{kol}+GE_kZ_{kos}$ $W^*_{kol}$=new weight value for neuron-like unit k of the outer layer.

$W_{kol}$=actual weight value obtained for neuron-like unit k of the outer layer.

G=gain factor $Z_{kos}$=actual output signal of neuron-like unit k of output layer.

$D_{kos}$=desired output signal of neuron-like unit k of output layer.

$E_k=Z_{kos}(1-Z_{kos})(D_{kos}-Z_{kos})$, (this is an error term corresponding to neuron-like unit k of outer layer).

For the hidden layer:

$W^*_{jhl}=W_{jhl}+GE_jY_{jos}$ $W^*_{jhl}$=new weight value for neuron-like unit j of the hidden layer.

$W_{jhl}$=actual weight value obtained for neuron-like unit j of the hidden layer.

G=gain factor $Y_{jos}$=actual output signal of nueron-like unit j of hidden layer.

$E_j=Y_{jos}(1-Y_{jos})\ _kE_k-W_{kol}$, (this an error term corresponding to neuron-like unit J of hidden layer over all k units).

For the input layer:

$W^*_{iil}=W_{iil}+GE_iX_{ios}$ $W^*_{iil}$=new weight value for neuron-like unit i of input layer.

$W_{iil}$=actual weight value obtained for neuron-like unit i of input layer.

G=gain factor $X_{ios}$=actual output signal of nueron-like unit i of input layer.

$E_i=X_{ios}(1-X_{ios})\ _jE_j-W_{jhl}$, (this is an error term corresponding to neuron-like unit i of input layer over all j units).

The process of entering new (or the same) empirical data into neural network as the input data is repeated and the output signal observed. If the output is again in error with what the known empirical output signal should be, the weights are adjusted again in the manner described above. This process continues until the output signals are substantially in accordance with the desired (empirical) output signal, then the weight of the modulators are fixed.

In a similar fashion, the NTF is used so that the soma-like units can produce output signals for increasing, decreasing, or maintaining cycle rate and for indicating ischemia, embolism and deep vein thrombosis. When these signals are substantially in accordance with the empirical known output signals, the weights of the modulators are fixed.

Upon fixing the weights of the modulators, predetermined solution space memory indicative of needing to increase, decrease,and maintain pressure, predetermined solution space memory indicative of needing to increase, decrease, and maintain cycle rate, and predetermined solution space memory indicative of normal and abnormal physiological conditions are established. The neural network is then trained and can make generalizations about input data by projecting input data into solution space memory which most closely corresponds to that data.

While the preferred embodiment has employed the neural network to carry out the invention, it is conceived that other means, such as a statistical program, might be used instead of or in conjunction with the neural network. It is also to be noted that several pumping apparatuses can be used and operated by the same neural network with the capability of delivering pressure to each area on an as needed basis. It is conceived that many variations, modifications and derivatives of the present invention are possible and the preferred embodiment set for the above is not meant to be limiting of the full scope of the invention.

What is claimed is:

1. A medical pumping apparatus, comprising:

means for applying pressure to a body part;

means for sensing blood fill status in the body part and generating a blood fill status signal in response thereto;

means for receiving and manipulating said blood fill status signal to produce an output signal, wherein said receiving and manipulating means includes neural network means for producing a generalization about said blood fill status signal, said generalization used to form said output signal, and wherein said neural network means includes a predetermined solution space memory indicative of needing to increase pressure, a predetermined solution space memory indicative of needing to decrease pressure, and a predetermined solution space indicative of needing to maintain pressure, and wherein said neural network means performs said generalization by projecting said blood fill status signal into one of said solution space memory; and means operatively associated with said receiving and manipulating means for controlling said pressure means in accordance with said output signal.

2. The apparatus of claim 1, which further includes means operatively connected to said receiving and manipulating means for sensing blood flow rate in the body part and generating a blood flow rate signal in response thereto to allow said neural network means to produce a generalization about said blood flow rate signal, and wherein said generalizations of said blood fill status and said blood flow rate signal are used to form said output signal.

3. The apparatus of claim 1, wherein said sensing means includes impedance sensing means for sensing impedance across the body part.

4. The apparatus of claim 1, wherein said sensing means further includes light reflective rheology sensing means for sensing blood flow across the body part.

5. The apparatus of claim 1, wherein said neural network comprises:

an input layer having a plurality of neuron-like units, wherein each neuron-like unit includes a receiving channel for receiving said blood fill status signal, wherein said receiving channel includes predetermined means for modulating said blood fill status signal;

a hidden layer having a plurality of neuron-like units individually receptively connected to each of said units of said input layer, wherein each connection includes predetermined means for modulating each connection between said input layer and said hidden layer; and an output layer having a plurality of neuron-like units individually receptively connected to each of said units of said hidden layer, wherein each connection includes predetermined means for modulating each connection between said hidden layer and said output layer, and wherein each unit of said output layer includes an outgoing channel for projecting the modulated blood fill status signal into at least one of said solution space memory.

6. The apparatus of claim 5, which further includes means operatively connected to said neural network for displaying said modulated signal.

7. The apparatus of claim 1, wherein said control means includes a control circuit responsive to said neural network and which controls pressure and cycle rate of said pressure means.

8. The apparatus of claim 7, wherein said control circuit controls said pressure means to synchronize the application of pressure and cycle rate with the maximum blood fill status.

9. The apparatus of claim 1, wherein said pressure application means includes:

an inflatable boot having an inflatable bladder shaped to conform to a human foot, a plate connected to said bladder and adapted to longitudinally extend along the sole of the foot, a surface conformable member disposed on said plate and between said plate and the sole of the foot, valve means integrally formed with said bladder through which a pneumatic pressure passes, and means for securing the bladder to the foot; and a pumping apparatus operatively connected to said boot, wherein said pumping apparatus is operatively connected to said control means and which delivers said pneumatic pressure to said boot.

10. The apparatus of claim 9, wherein said boot is connected to said sensing means such that said sensing means are disposed adjacent to the dorsum and the sole of the foot.

11. The apparatus of claim 9, wherein said boot is connected to said sensing means such that said sensing means are disposed adjacent to the heel and the sole of the foot.

12. A medical pumping apparatus, comprising:

means for applying pressure to a body part;

means for sensing blood fill status in the body part and generating a blood fill status signal in response thereto;

means for receiving and manipulating said blood fill status signal to produce an output signal, wherein said receiving and manipulating means includes neural network means for producing a generalization about said blood fill status signal, said generalization used to form said output signal, and wherein said neural network means includes a predetermined solution space memory indicative of needing to increase pressure application rate, a predetermined solution space memory indicative of needing to decrease pressure application rate, and a predetermined solution space indicative of needing to maintain pressure application rate, and wherein said neural network means performs said generalization by projecting said blood fill status signal into one of said solution space memory; and means operatively associated with said receiving and manipulating means for controlling said pressure means in accordance with said output signal.

13. The apparatus of claim 12, wherein said sensing means includes impedance sensing means for sensing impedance across the body part.

14. The apparatus of claim 12, wherein said sensing means includes light reflective rheology sensing means for sensing blood flow across the body part.

15. The apparatus of claim 12, wherein said neural network comprises:

an input layer having a plurality of neuron-like units, wherein each neuron-like unit includes a receiving channel for receiving said blood fill status signal, wherein said receiving channel includes predetermined means for modulating said blood fill status signal;

a hidden layer having a plurality of neuron-like units individually receptively connected to each of said units of said input layer, wherein each connection includes predetermined means for modulating each connection between said input layer and said hidden layer; and an output layer having a plurality of neuron-like units individually receptively connected to each of said units of said hidden layer, wherein each connection includes predetermined means for modulating each connection between said hidden layer and said output layer, and wherein each unit of said output layer includes an outgoing channel for projecting the modulated blood fill status signal into at least one of said solution space memory.

16. The apparatus of claim 15, which further includes means operatively connected to said neural network for displaying said modulated signal.

17. The apparatus of claim 12, wherein said control means includes a control circuit responsive to said neural network and which controls pressure and cycle rate of said pressure means.

18. The apparatus of claim 17, wherein said control circuit controls said pressure means to synchronize the application of pressure and cycle rate with the maximum blood fill status.

19. The apparatus of claim 12, wherein said pressure application means includes:

an inflatable boot having an inflatable bladder shaped to conform to a human foot, a plate connected to said bladder and adapted to longitudinally extend along the sole of the foot, a surface conformable member disposed on said plate and between said plate and the sole of the foot, valve means integrally formed with said bladder through which a pneumatic pressure passes, and means for securing the bladder to the foot; and a pumping apparatus operatively connected to said boot, wherein said pumping apparatus is operatively connected to said control means and which delivers said pneumatic pressure to said boot.

20. The apparatus of claim 19, wherein said boot is connected to said sensing means such that said sensing means are disposed adjacent to the dorsum and the sole of the foot.

21. The apparatus of claim 19, wherein said boot is connected to said sensing means such that said sensing means are disposed adjacent to the heel and the sole of the foot.

22. The apparatus of claim 12, which further includes means operatively connected to said receiving and manipulating means for sensing blood flow rate in the body part and generating a blood flow rate signal in response thereto to allow said neural network means to produce a generalization about said blood flow rate signal, and wherein said generalizations of said blood fill status and said blood flow rate signal are used to form said output signal.

23. A medical pumping apparatus, comprising:

means for applying pressure to a body part;

means for sensing blood fill status in the body part and generating a blood fill status signal in response thereto;

means for receiving and manipulating said blood fill status signal to produce an output signal, wherein said receiving and manipulating means includes neural network means for producing a generalization about said blood fill status signal, said generalization used to form said output signal, and wherein said neural network means includes a predetermined solution space memory indicative of normal physiological conditions and a predetermined solution space indicative of abnormal physiological conditions, and wherein said neural network means performs said generalization by projecting said blood fill status signal into one of said solution space memory; and means operatively associated with said receiving and manipulating means for controlling said pressure means in accordance with said output signal.

24. The apparatus of claim 23, wherein said abnormal physiological solution space is indicative of deep vein thrombosis.

25. The apparatus of claim 23, wherein said abnormal physiological solution space is indicative of ischemia.

26. The apparatus of claim 23, wherein said abnormal physiological solution space is indicative of venous insufficiency.

27. The apparatus of claim 23, wherein said sensing means includes impedance sensing means for sensing impedance across the body part.

28. The apparatus of claim 23, wherein said sensing means includes light reflective rheology sensing means for sending blood flow across the body part.

29. The apparatus of claim 23, wherein said neural network comprises:

an input layer having a plurality of neuron-like units, wherein each neuron-like unit includes a receiving channel for receiving said blood fill status signal, wherein said receiving channel includes predetermined means for modulating said blood fill status signal;

a hidden layer having a plurality of neuron-like units individually receptively connected to each of said units of said input layer, wherein each connection includes predetermined means for modulating each connection between said input layer and said hidden layer; and an output layer having a plurality of neuron-like units individually receptively connected to each of said units of said hidden layer, wherein each connection includes predetermined means for modulating each connection between said hidden layer and said output layer, and wherein each unit of said output layer includes an outgoing channel for projecting the modulated blood fill status signal into at least one of said solution space memory.

30. The apparatus of claim 29, which further includes means operatively connected to said neural network for displaying said modulated signal.

31. The apparatus of claim 23, wherein said control means includes a control circuit responsive to said neural network and which controls pressure and cycle rate of said pressure means.

32. The apparatus of claim 31, wherein said control circuit controls said pressure means to synchronize the application of pressure and cycle rate with the maximum blood fill status.

33. The apparatus of claim 23, wherein said pressure application means includes:

an inflatable boot having an inflatable bladder shaped to conform to a human foot, a plate connected to said bladder and adapted to longitudinally extend along the sole of the foot, a surface conformable member disposed on said plate and between said plate and the sole of the foot, valve means integrally formed with said bladder through which a pneumatic pressure passes, and means for securing the bladder to the foot; and a pumping apparatus operatively connected to said boot, wherein said pumping apparatus is operatively connected to said control means and which delivers said pneumatic pressure to said boot.

34. The apparatus of claim 33, wherein said boot is connected to said sensing means such that said sensing means are disposed adjacent to the dorsum and the sole of the foot.

35. The apparatus of claim 34, wherein said boot is connected to said sensing means such that said sensing means are disposed adjacent to the heel and the sole of the foot.

36. The apparatus of claim 23, which further includes means operatively connected to said receiving and manipulating means for sensing blood flow rate in the body part and generating a blood flow rate signal in response thereto to allow said neural network means to produce a generalization about said blood flow rate signal, and wherein said generalizations of said blood fill status and said blood flow rate signal are used to form said output signal.

* * * * *

UNITED STATES PATENT AND TRADEMARK OFFICE

CERTIFICATE OF CORRECTION

PATENT NO. : 5,396,896

DATED : March 14, 1995

INVENTOR(S) : David M. Tumey et al

It is certified that error appears in the above-indentified patent and that said Letters Patent is hereby corrected as shown below:

Column 11, line 42, "sending blood flow" should be --sensing blood flow--.

Signed and Sealed this

Sixteenth Day of January, 1996

Attest:

Bruce Lehman

BRUCE LEHMAN

*Attesting Officer* *Commissioner of Patents and Trademarks*